United States Patent
DiMatteo et al.

(10) Patent No.: US 7,413,173 B2
(45) Date of Patent: Aug. 19, 2008

(54) MOLDED WATER CHAMBER BASE PLATE FOR USE IN A HUMIDIFIER AND VENTILATOR ASSEMBLY

(75) Inventors: Mark DiMatteo, Irwin, PA (US); William Perroz, Jr., Vandergrift, PA (US)

(73) Assignee: RIC Investments, LLC, Wilmington, DE (US)

( * ) Notice: Subject to any disclaimer, the term of this patent is extended or adjusted under 35 U.S.C. 154(b) by 51 days.

(21) Appl. No.: 11/212,228

(22) Filed: Aug. 26, 2005

(65) Prior Publication Data
US 2006/0055069 A1    Mar. 16, 2006

Related U.S. Application Data

(60) Provisional application No. 60/609,154, filed on Sep. 10, 2004.

(51) Int. Cl.
  *B01F 3/04* (2006.01)
(52) U.S. Cl. ............... 261/142; 261/30; 261/119.1; 128/203.27; 128/204.18; 392/405
(58) Field of Classification Search ............ 261/30, 261/119.1, 142, DIG. 65; 128/203.12, 203.17, 128/203.26, 203.27, 204.14, 204.18; 392/402, 392/405
See application file for complete search history.

(56) References Cited

U.S. PATENT DOCUMENTS

| | | | | |
|---|---|---|---|---|
| 5,062,145 | A | * | 10/1991 | Zwaan et al. ............ 392/396 |
| 5,367,604 | A | * | 11/1994 | Murray .................... 392/394 |
| 5,598,502 | A | | 1/1997 | Takahashi et al. |
| 5,673,687 | A | | 10/1997 | Dobson et al. |
| 6,115,539 | A | | 9/2000 | Cohn |
| 6,321,570 | B1 | | 11/2001 | DeVries, Jr. et al. |
| 6,349,722 | B1 | | 2/2002 | Gradon et al. |
| 6,503,584 | B1 | | 1/2003 | McAlister |

OTHER PUBLICATIONS

LNP Engineering Plastics, Konduit™ spec sheet, Aug. 2005.
LNP Engineering Plastics, "LNP Introduces First-Ever Line of Thermally Conductive Compounds", Aug. 2005.
Respironics, Inc., REMstar® Plus Pro product brochure, 2001.
Respironics, Inc., REMstar® Auto product brochure, 2002.

* cited by examiner

*Primary Examiner*—Scott Bushey
(74) *Attorney, Agent, or Firm*—Timothy A. Nathan (57) ABSTRACT

A molded base plate for use in a humidifier and ventilation assembly is disclosed. The base plate is connected to a cover which forms the water chamber of the humidifier. A thermally conductive material is used in the molding process of the base plate so that heat applied to the base plate is conducted into the water.

21 Claims, 7 Drawing Sheets

MOLDED WATER CHAMBER BASE PLATE FOR USE IN A HUMIDIFIER AND VENTILATOR ASSEMBLY

CROSS-REFERENCE TO RELATED APPLICATIONS

Under the provisions of 35 U.S.C. § 119(e), this application claims the benefit of U.S. Provisional Application Ser. No. 60/609,154, filed Sep. 10, 2004.

BACKGROUND OF THE INVENTION

1. Field of the Invention

The present invention pertains to heated humidifiers, and in particular, to heated humidifiers with water chambers.

2. Description of the Related Art

Many individuals suffer from sleep apnea and other related diseases which result in episodic upper airway obstruction during sleep. As a consequence, there is repeated interruption of sleep in the patient. Positive airway pressure (PAP) devices have been developed to treat this disorder. A typical PAP device comprises a flow generator (e.g., a blower) that delivers gas via a delivery conduit to a user interface, such as a mask. It is also known to deliver the PAP pressure as a continuous positive airway pressure (CPAP), a variable airway pressure, such as a bi-level pressure that varies with the patient's respiratory cycle, or an auto-titrating pressure that varies with the monitored condition of the patient. Pressure support therapies are also provided to treat other medical and respiratory disorders, such as Cheynes-Stokes respiration, congestive heart failure, and stroke.

Providing positive airway pressure to such patients is well known in the art. However, it has been found that using dry pressurized air is uncomfortable to the user. Over time, breathing such air will dry out the patient's throat, nasal passage, and mucus membranes resulting in discomfort and pain. In order to overcome this problem many ventilators include a humidifier to add water vapor to the air inhaled by the patient. One such device exemplary of the art is disclosed in U.S. Pat. No. 5,673,687 to Dobson et al. ("the '687 patent"). This device includes a ventilator, a passive humidifier, and a delivery conduit. The passive humidifier disclosed in this patent has a reservoir filled with water and a corresponding lid. The humidifier is connected between the outlet of the ventilator and the air delivery conduit. As the patient breaths, air is forced out of the ventilator and passes over water contained in the reservoir. Water vapor is passively entrained with the dry air as the water naturally evaporates within the reservoir. The humidified air then passes through the delivery conduit and inhaled by the patient.

It was found desirable to increase the amount of water vapor entrained with the air. One such device capable of accomplishing this goal is the humidifier described in U.S. Pat. No. 6,349,722 to Gradon et al. The humidifier disclosed in this patent has a water chamber with a plastic top and a metal bottom. Forming the water chamber from two separate parts allows for easy access to the interior of the chamber and cleaning. The chamber sits on top of a heater plate. Active humidification occurs as the temperature of the heater plate increases above ambient temperature. The heat generated by the heater plate raises the temperature of the water contained in the chamber and thus accelerates the rate of evaporation. Aluminum is often used to form the metal bottom because of its low cost, and high thermal conductivity. The metal bottom is typically formed by stamping a sheet of aluminum. A rubber seal is then overmolded about the metal bottom in order to create a fluid tight seal with the plastic top.

Although such devices have advanced the art, several improvements can still be made. In the case of an aluminum metal bottom, it can become dinged and dented since the material has little shape memory. Secondly, the aluminum metal bottom is used in a humid environment and thus prone to corrosion and pitting. Careful application of anodizing or other similar processes is needed to control the degradation of the metal bottom. Another feature of these devices that could be improved upon is the manufacturing process. Typically, the metal bottom is formed by stamping and cutting a sheet of aluminum. Next, a fluid-tight seal is formed between the metal bottom and the plastic top by overmolding a seal about the metal bottom. The metal bottom is formed by stamping and cutting thin sheet aluminum in multiple steps using a progressive die. The part is then transferred to a second machine for overmolding the seal. This is a time consuming processing method and requires expertise in two very different manufacturing technologies.

SUMMARY OF THE INVENTION

In accordance with the broad teachings of the invention a water chamber base plate is disclosed that is used in a ventilator and humidifier assembly to provide humid, pressurized air to a user. The ventilator has a water chamber with a base plate. The base plate includes a body portion which interfaces with a heat emitting heater plate, and is formed from a thermally conductive composite material. The thermally conductive composite material facilitates conductive heating of the water contained within the water chamber. Another aspect of the present invention is its method of manufacture. The water chamber is formed by molding the body portion of the water chamber. Next, a gasket is then molded about the body of the water chamber. Finally, a cover is molded and attached to the body to provide a substantially fluid-tight water chamber.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
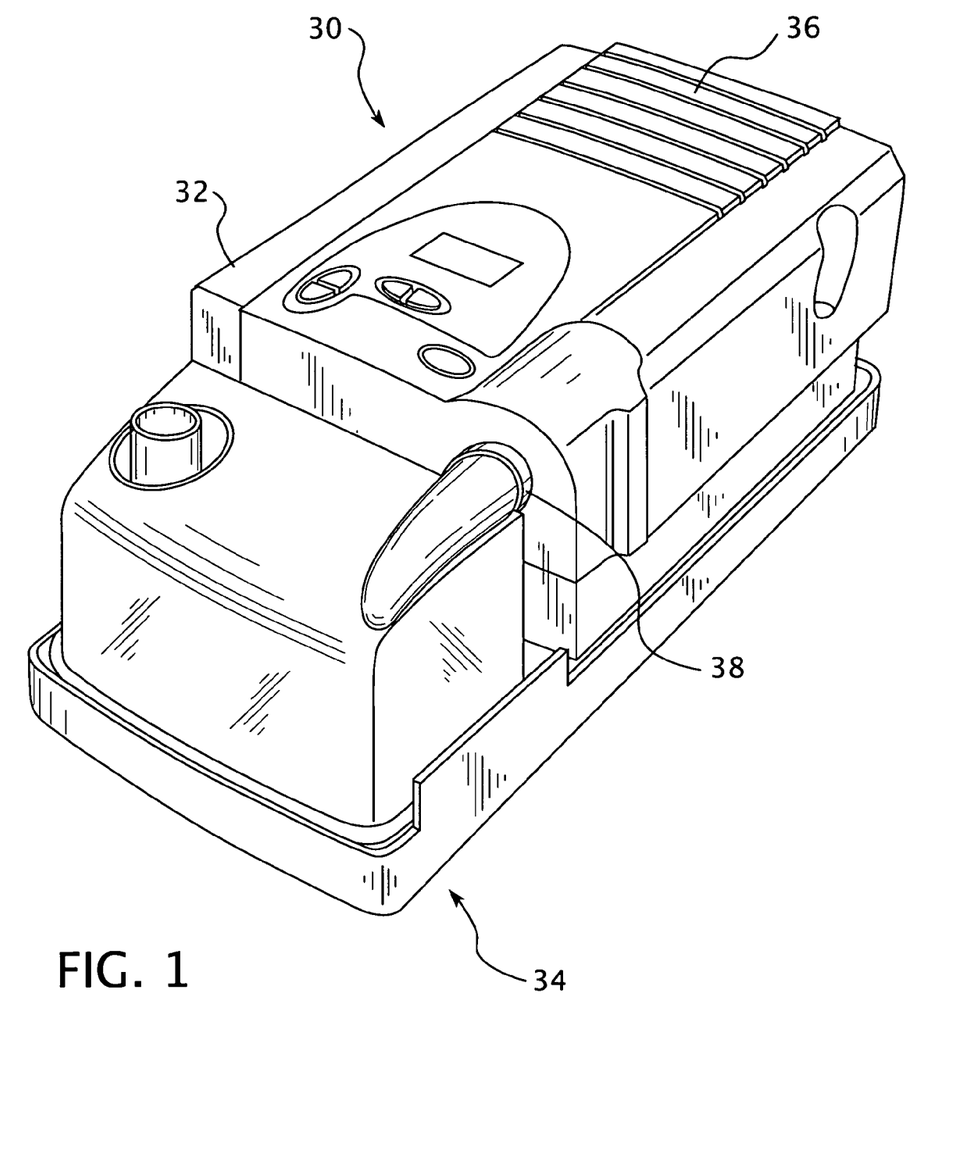
FIG. 1 is a top perspective view of a humidifier and ventilator assembly.

FIG. 1 schematically illustrates an exemplary embodiment of a humidifier and ventilator assembly 30 according to the principles of the present invention. The assembly includes a ventilator 32 and a humidifier 34. As used herein, ventilator 32 may be a pressure support system or PAP device. Generally, this assembly is used to provide moist, pressurized air to a user. Air is pressurized by the ventilator 32, humidified by humidifier 34, and then delivered to the user by a delivery conduit, not shown, that is connected to a patient interface, not shown. Ventilator 32 has an air intake 36 and an air outlet 38. The ventilator receives unpressurized air via air intake 36, pressurizes the air, and then forces the air out air outlet 38.

Figure 2:
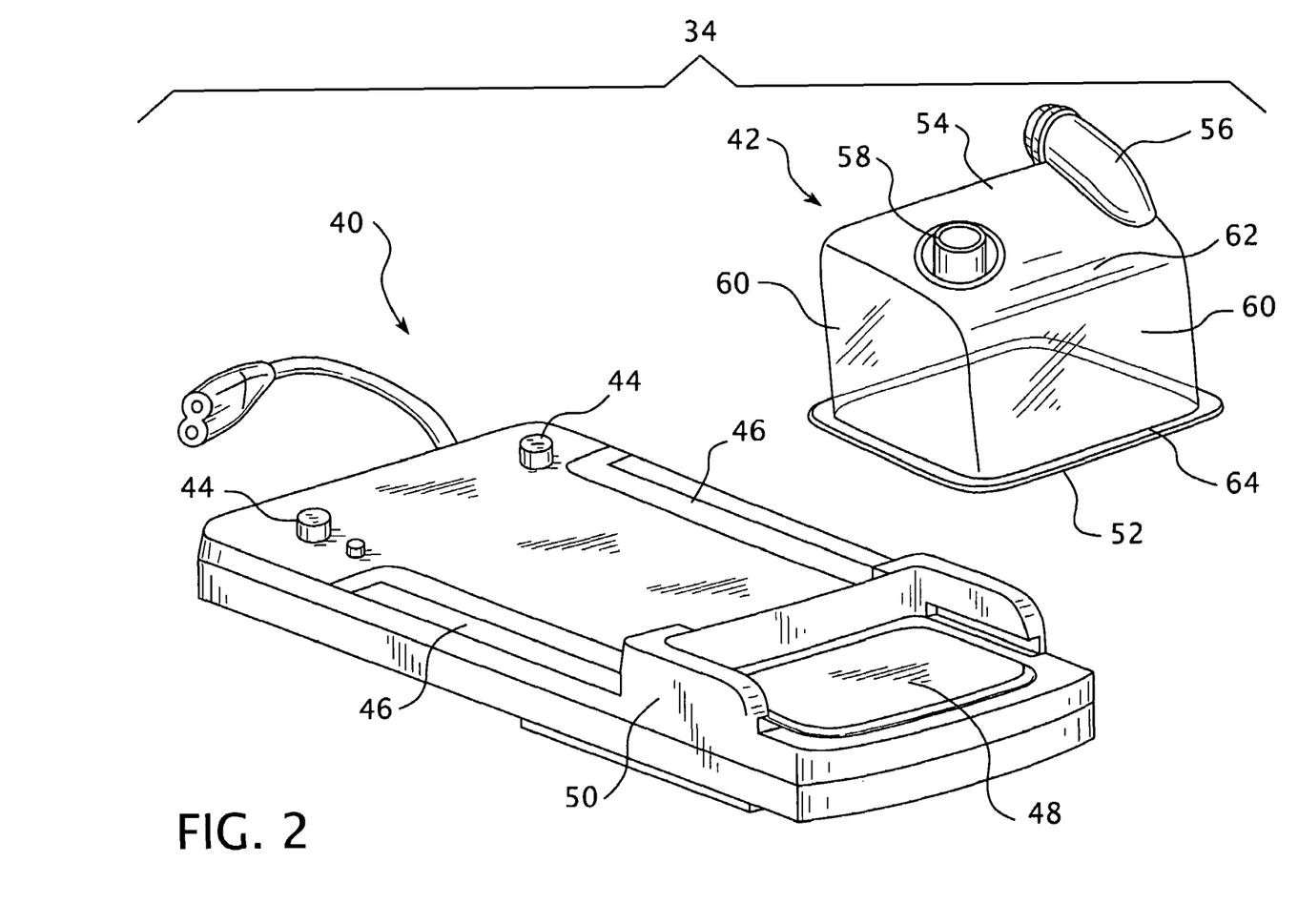
FIG. 2 is an exploded top perspective view of the humidifier and ventilator assembly.

As seen in FIG. 2, the humidifier has a ventilator dock 40 and a removable water chamber 42. The ventilator dock is configured to couple with ventilator 32. Ventilator dock 40 has bosses 44 which engage recesses, not shown, on ventilator 32. The ventilator dock also has channels 46 that engage with projecting portions, not shown, on the ventilator. Together bosses 44 and channels 46 operate to hold ventilator 32 in place on ventilator dock 40 of the humidifier. The ventilator dock also has a heater plate 48 surrounded by a ledge 50. Heater plate 48 is used to deliver thermal energy to the removable water chamber 42. Ledge 50 provides a barrier to prevent unintentional contact with heater plate 48 by the user or other items present in the user's environment. Heat is generated by a resistive heat element, not shown. However, any device capable of raising the temperature of the water may be used.

Water chamber 42 includes a base plate 52 and a cover 54 removably sealed with base plate 52. Cover 54 is removably sealed with base plate 52 so that water chamber 42 can retain water and yet be easily separated for cleaning and maintenance. However, the cover 54 could also be fixedly attached to the base plate. The present invention has also been described for use with water retained within water chamber 42 to create water vapor for inhalation by the user. However, it is also contemplated that various other fluids could be used in replace of, or in combination with, the water. Furthermore, additives could also be placed in the chamber as well and suspended in the fluid.

Cover 54 has an inlet port 56 and an outlet port 58. The inlet port is connected to the air outlet on ventilator 32. The outlet port on the cover is connected to the delivery conduit, not shown, to deliver the humid, pressurized air to the user. Cover 54 has four side walls 60 terminating at an upper wall 62. Side walls 60 define an opening 64. The cover is formed from acrylic plastic. However, various other materials can be used without departing from the teachings of the present invention.

Figure 3:
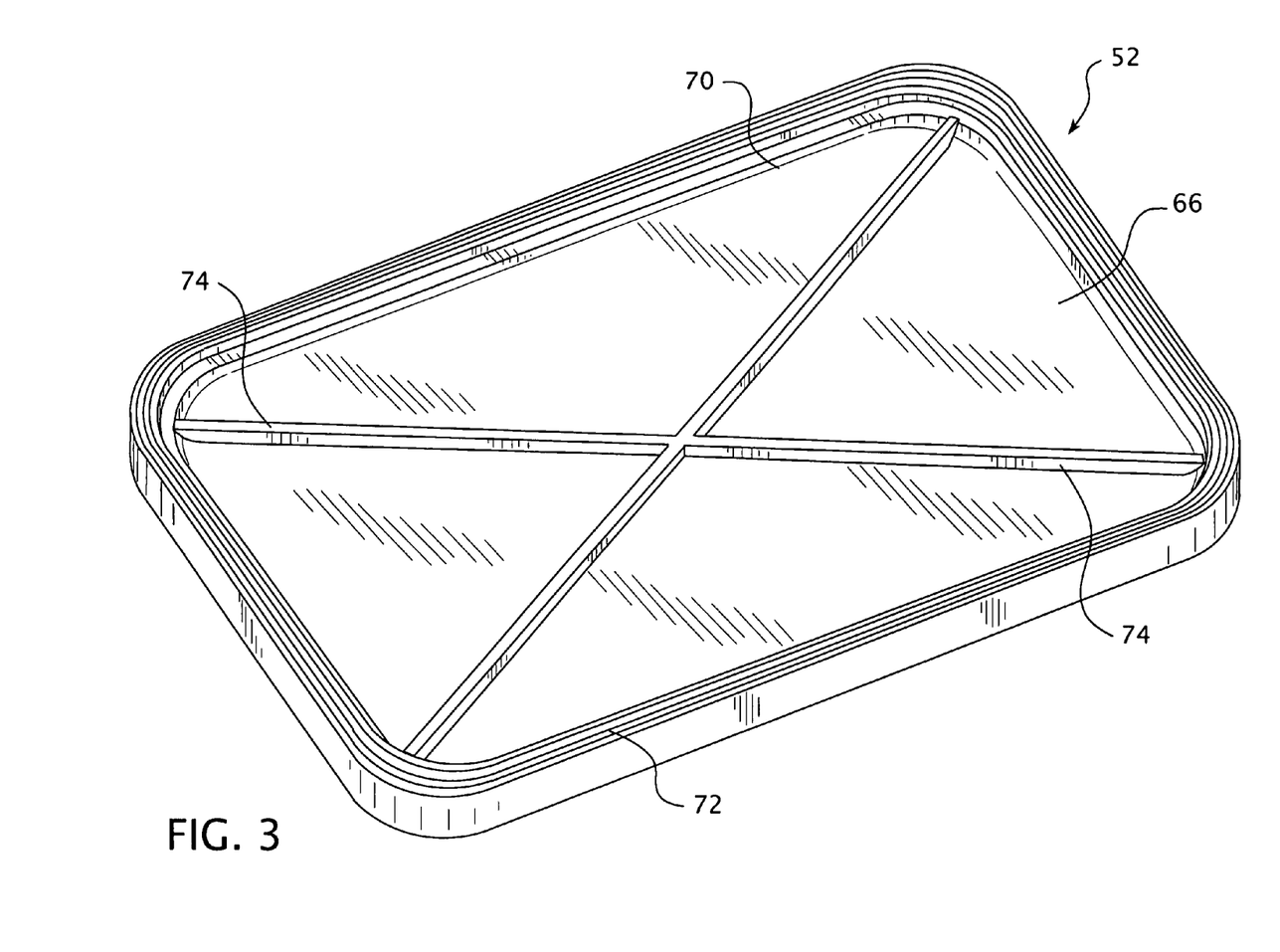
FIG. 3 is a top perspective view of a base plate.
Figure 4:
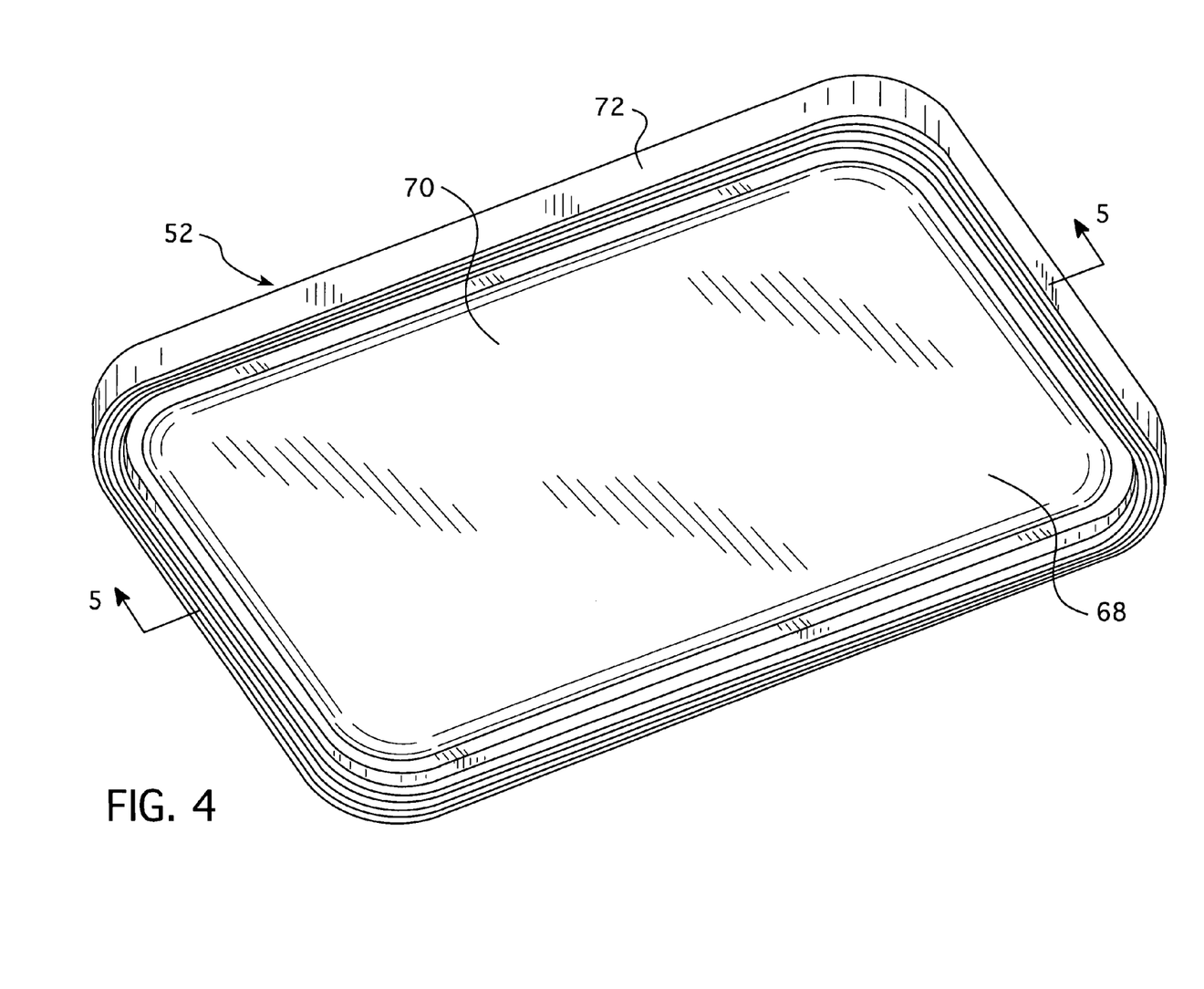
FIG. 4 is a bottom perspective view of the base plate.

As best appreciated with reference to FIGS. 3 and 4, base plate 52 has a first surface 66 and a second surface 68 defining a body 70. In one embodiment, base plate 52 also has a gasket 72 to provide a fluid-tight seal when base plate 52 is coupled to cover 54. Gasket 72 is formed from silicon. However, any material capable of providing a substantially fluid-tight seal could be used without departing from the scope of the present invention. The first surface of the base plate also includes ribs 74. The ribs are located on body 70 to provide additional structural rigidity to base plate 52.

One unique aspect of the present invention is that base plate 52 is formed from a thermally conductive composite material. Any thermally conductive composite material may be used in accordance with the present invention. Generally, composite materials are comprised of a plastic resin filled with an additive. A number of plastic resins may be used such as nylon, polypropylene, polyphenylsulfone, polyphenylene sulfide, or polyurethane. In addition, a variety of different thermally conductive additives are known such as graphite, and carbon. Ceramic materials having thermal conductivity such as aluminum nitride, or boron nitride could also be used. Using a composite material with ceramic additives may provide the additional benefit of being both electrically insulative and thermally conductive. However, such ceramic materials tend to have lower thermal conductivity. Accordingly, based on the type and amount of additive utilized, the characteristics of the base plate can be modified to suit particular applications. In the preferred embodiment of the present invention, the composite is comprised of polyphenylene sulfide and carbon.

One benefit of using a thermally conductive plastic material is that it can be molded rather than being stamped. Stamping the body of the base plate requires the use of a multi-step progressive die manufacturing process. After the body is stamped, the part is then overmolded with a seal. This process uses multi-step, time-consuming process to stamp and cut the details of the base plate. In contrast, the base plate of the present invention can be molded in a double-step molding process using only two molds.

Fine details can be molded into the base plate whereas the details and features that can be stamped into a sheet of aluminum are limited. Because a stamped part is formed from sheet material, the material thickness cannot be appreciably varied. With respect to plastic parts, mold can be manufactured with any number of thickness variations. Finally, molded plastic products are not prone to corrosion.

Figure 5:
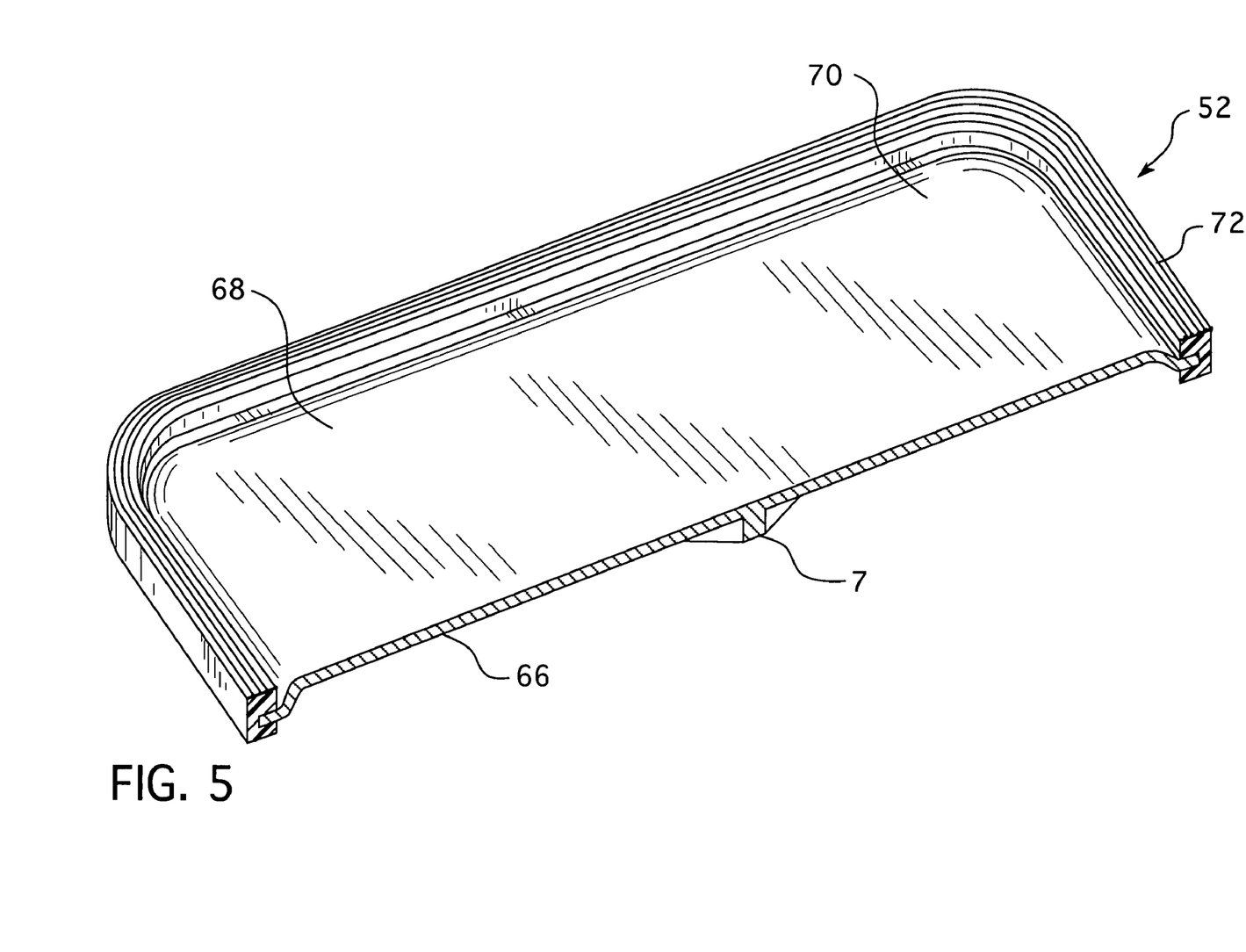
FIG. 5 is a cross-sectional bottom perspective view of the base plate along line 5-5 of FIG. 4.

Another unique feature of the present invention is the method by which the gasket 72 is attached to base plate 52. Once body 70 has been formed, gasket 72 can be molded to body 70, as shown in FIG. 5. Advantageously, this can be accomplished by a multi-polymer injection molding process such as double-shot injection molding. As used herein, double-shot injection molding shall be interpreted to mean an injection molding process wherein a first part is molded in a first mold with one material and then cooled. The first part is then used as an insert in a second mold which is injection molded with a second material. The completed part is then cooled and removed from the second mold. Although gasket 72 has been preferably described as being molded to base plate 52, it could also be a separate part attached with an adhesive or other similar material without departing from the teachings of the present invention.

Figure 6A:
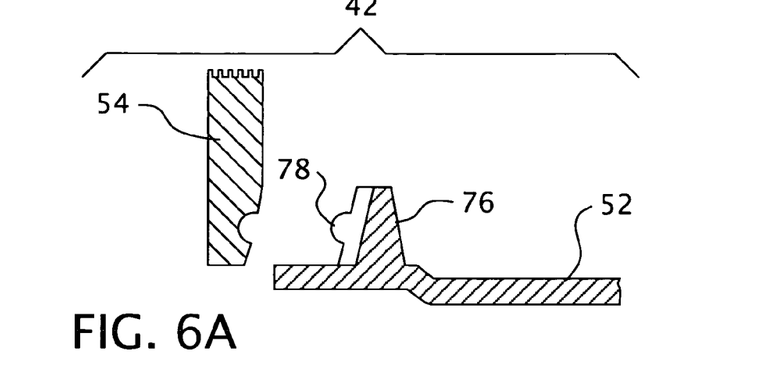
FIG. 6A is a partial cross-sectional elevational view of an alternative embodiment of the base plate.

The present invention also contemplates various other embodiments. As shown in FIG. 6A, base plate 52 may also include a peripheral ridge 76 against which gasket 72 is formed to provide a support surface for gasket 72. In addition to molding details into base plate 52, gasket 72 can also be molded with various other details such as a bead 78 to provide a tight fit between the gasket and the cover.

Figures 6B, 6C:
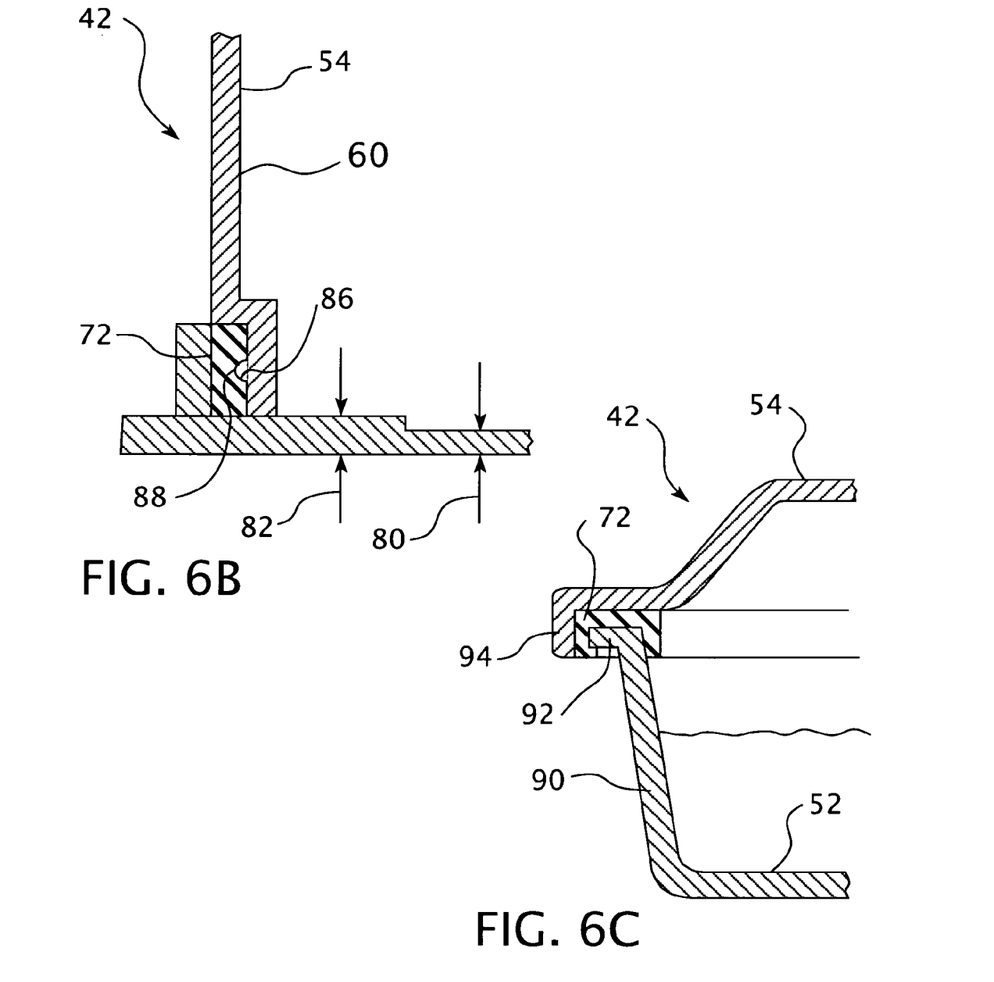
FIG. 6B is a partial cross-sectional elevational view of a second alternative embodiment of the base plate.
FIG. 6C is a partial cross-sectional elevational view of a third alternative embodiment of the base plate.

In a second embodiment, base plate 52 can be molded having varied wall thicknesses between first surface 66 and second surface 68. The wall thickness may be formed relatively thinner in certain regions to increase thermal conductivity, or may be formed relatively thicker in certain regions to increase the insulation characteristics of the base plate. As seen in FIG. 6B, first wall thickness 80 is less than second wall thickness 82. In this embodiment, base plate 52 is also formed with flange 84. Gasket 72 is molded to flange 84 and has a recess 86 which engages an annular bead 88 of side wall 60 to provide a tight fit between the gasket and the cover.

In a third embodiment shown in FIG. 6C, base plate 54 has walls 90 which terminate at a lip 92. The water chamber of this embodiment includes a cover 54 terminating at a skirt 94 which overlays the lip. Base plate 54 has a gasket 72 attached to lip 92 which seals cover 54 with base plate 52.

Figure 6D:
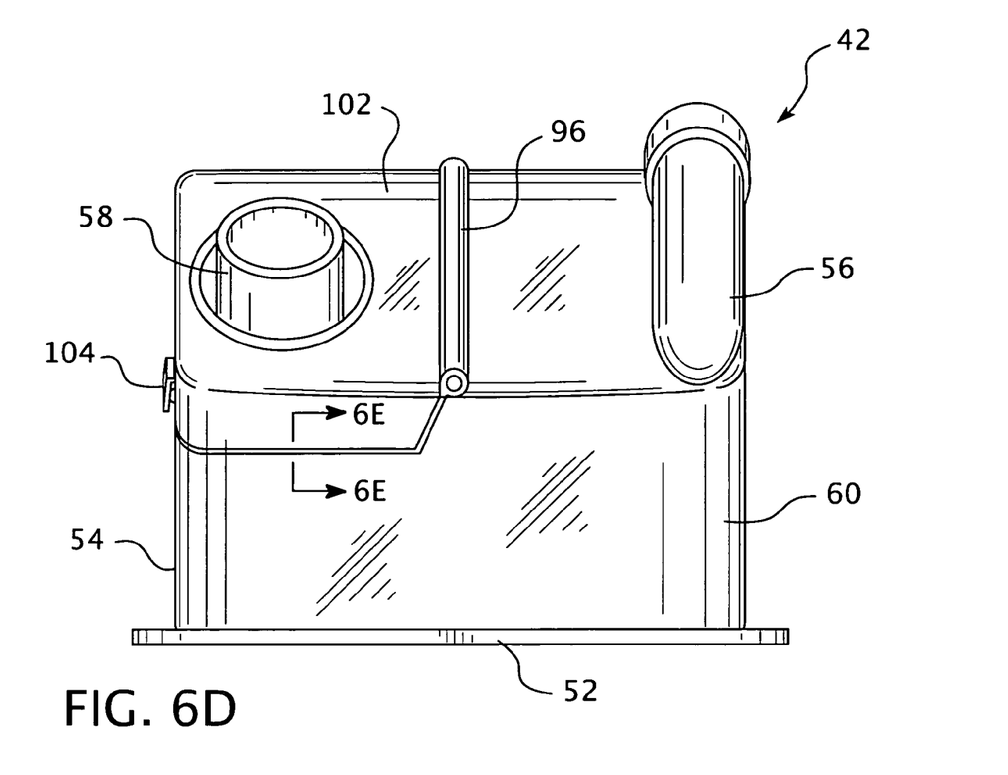
FIG. 6D is a front elevational of view of a fourth alternative embodiment of the base plate.
Figure 6E:
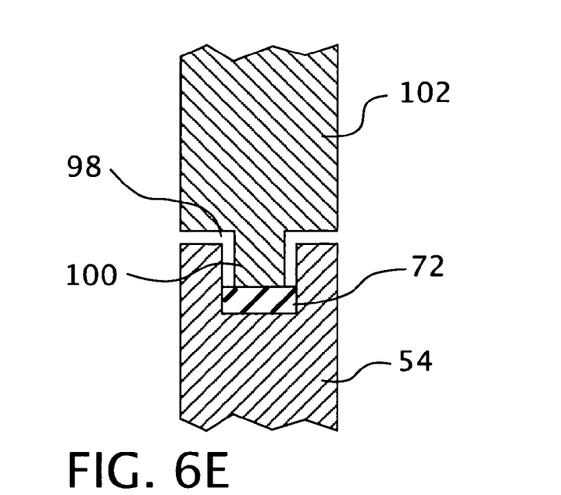
FIG. 6E is a cross-sectional view of the fourth alternative embodiment of the base plate along line 6E-6E of FIG. 6D.

In a fourth alternative embodiment, as shown in FIG. 6D, cover 54 is attached to base plate 52 and has a lid 102 attached with a pivot hinge 96 to the cover 54 such that the lid 102 can be pivoted between an open position and a closed position. When in the closed position, the lid 102 is held in place by latch 104. The lid 102 includes air outlet 38. Base plate 52 is press-fit to cover 54. Lid 102 also includes a channel 98 into which a projection 100 on cover 54 is inserted. Channel 98 also includes gasket 72 such that when cover 54 is in the closed position gasket 72 seals with projection 100 as seen in FIG. 6E.

The present invention also contemplates a method of manufacturing a water chamber using a double-shot molding process. First, body 70 of base plate 54 is molded in a first mold by injecting a thermally conductive composite material into the mold and then cooling the body. Next, the body is removed from the first mold once it has cooled sufficiently and inserted into a second mold. A second material is then injected into the second mold to form a seal about body 70. The base plate is then cooled. Once the second material has cooled sufficiently, the base plate 52 is removed from the second mold. Cover 54 is formed in a third mold by injecting material into the third mold. The cover is then cooled and removed from the third mold. The base plate is then fitted to the cover to form the water chamber. This configuration allows the base plate and the cover can be removably attached together. However, the base plate and cover could also be fixedly attached together with an adhesive or other similar material. Moreover, the base plate and cover could also be formed together as a single part.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A water chamber for use in a heated humidifier having a heater plate having a size and shape, the water chamber comprising:
    a base plate having a body, the body portion being formed from a thermally conductive composite material, the body of the base plate including a first surface and a second surface, the second surface is supported by the heater plate such that heat may be conducted from the heater and through the base plate, the body portion of the base plate is separate from the heater plate and substantially the same size and shape as the size and shape of the heater plate; and
    a cover connected to the base plate.

2. The water chamber as recited in claim 1, wherein the thermally conductive material comprises plastic resin and a thermally conductive additive.

3. The water chamber as recited in claim 2, wherein the thermally conductive additive is selected from the group comprising graphite or carbon.

4. The water chamber as recited in claim 2, wherein the thermally conductive additive is selected from the group comprising aluminum nitride or boron nitride.

5. The water chamber as recited in claim 1, wherein the base plate and cover are sealingly engaged.

6. The water chamber as recited in claim 1, wherein the base plate further comprises at least one rib.

7. The water chamber as recited in claim 1, wherein the base plate further comprises a lip extending from the body.

8. The water chamber as recited in claim 5, wherein the base plate includes a bead and the cover includes a corresponding recess sealingly engaging the bead.

9. The water chamber as recited in claim 5, wherein the base plate includes a recess and the cover includes a bead.

10. The water chamber as recited in claim 1, wherein the cover further includes a pivotable lid.

11. A humidifier for use with a ventilator, the humidifier comprising:
    a ventilator dock;
    a heater plate adjacent the ventilator dock;
    a water chamber adjacent the heater plate, the water chamber having a base plate, the base plate including a body portion formed from a thermally conductive composite material and a cover attached to the base plate, the body portion of the base plate including a first surface and a second surface, the second surface is supported by the heater plate such that heat may be conducted from the heater and through the base plate, the body portion of the base plate is separate from the heater plate and substantially the same size and shape of the heater plate.

12. The humidifier of claim 11, wherein the thermally conductive material comprises a plastic resin and a thermally conductive additive.

13. The humidifier of claim 12, wherein the thermally conductive additive is selected from the group comprising graphite or carbon.

14. The humidifier of claim 12, wherein the thermally conductive additive is selected from the group comprising aluminum nitride or boron nitride.

15. The humidifier of claim 14, wherein the base plate further comprises a seal.

16. The humidifier of claim 11, wherein the base plate further comprises at least one rib.

17. The humidifier as recited in claim 11, wherein the base plate further comprises a lip extending from the body.

18. The humidifier as recited in claim 15, wherein the base plate includes a bead and the cover includes a corresponding recess sealingly engaging the bead.

19. The humidifier as recited in claim 15, wherein the base plate includes a recess and the cover includes a bead.

20. The humidifier as recited in claim 11, wherein the cover further includes a pivotable lid.

21. A humidifier and ventilator assembly for use in delivering humid pressurized air to a user, the assembly comprising:
    a humidifier, the humidifier having a ventilator dock and a heater plate adjacent the ventilator dock, the humidifier also having a water chamber adjacent the heater plate, the water chamber having base plate, the base plate including a body portion formed from a thermally conductive composite material and a cover attached to the base plate, the water chamber having an inlet port and an outlet port, the body portion of the base plate including a first surface and a second surface, the second surface is supported by the heater plate such that heat may be conducted from the heater and through the base plate, the body portion of the base plate is separate from the heater plate and substantially the same size and shape as the size and shape of the heater plate;
    a ventilator having an air intake and an air outlet, the air outlet being connected to the inlet port of the water chamber.

* * * * *